United States Patent
Kasuto et al.

(10) Patent No.: US 9,512,393 B2
(45) Date of Patent: Dec. 6, 2016

(54) DEVICES AND METHODS FOR CULTURE OF CELLS

(71) Applicant: Pluristem Ltd., Haifa (IL)

(72) Inventors: Harel Kasuto, Kibbutz Yifat (IL);
Eytan Abraham, Frederick, MD (US);
Zami Aberman, Tel-Mond (IL)

(73) Assignee: Pluristem Ltd., Haifa (IL)

( * ) Notice: Subject to any disclaimer, the term of this patent is extended or adjusted under 35 U.S.C. 154(b) by 0 days.

(21) Appl. No.: 14/426,265

(22) PCT Filed: Aug. 31, 2013

(86) PCT No.: PCT/IB2013/058184
§ 371 (c)(1),
(2) Date: Mar. 5, 2015

(87) PCT Pub. No.: WO2014/037862
PCT Pub. Date: Mar. 13, 2014

(65) Prior Publication Data
US 2015/0232797 A1    Aug. 20, 2015

Related U.S. Application Data

(60) Provisional application No. 61/697,445, filed on Sep. 6, 2012.

(51) Int. Cl.
*C12M 3/00* (2006.01)
*C12M 1/00* (2006.01)

(52) U.S. Cl.
CPC .................................. *C12M 23/34* (2013.01)

(58) Field of Classification Search
CPC .................................................. C12N 2531/00
See application file for complete search history.

(56) References Cited

U.S. PATENT DOCUMENTS 4,144,126 A      3/1979   Burbidge
5,010,013 A *    4/1991   Serkes .................... C12M 23/08
                                                   215/383

(Continued)

FOREIGN PATENT DOCUMENTS

EP    0 967 273 A1   12/1999
EP    2 151 492 A1    2/2010

(Continued)

OTHER PUBLICATIONS

Kitagawa et al., Three-dimensional cell seeding and growth in radial-flow perfusion bioreactor for in vitro tissue reconstruction. Biotechnol Bioeng. Apr. 5, 2006;93(5):947-54.

(Continued)

*Primary Examiner* — Allison Fox
(74) *Attorney, Agent, or Firm* — Wolf, Greenfield & Sacks, P.C.

(57) ABSTRACT

Devices and methods for culture of cells are provided. The devices can comprise a three-dimensional body having multiple two-dimensional surfaces extending inwardly from a periphery of the three-dimensional body towards an interior of the three-dimensional body, wherein the multiple two-dimensional surfaces are configured to support monolayer growth of eukaryotic cells over at least a majority of or all of the surface area of the multiple two-dimensional surfaces.

23 Claims, 17 Drawing Sheets

(56) References Cited

U.S. PATENT DOCUMENTS

| | | | |
|---|---|---|---|
| 5,512,474 A | 4/1996 | Clapper et al. | |
| 5,629,186 A | 5/1997 | Yasukawa et al. | |
| 6,911,201 B1 | 6/2005 | Merchav et al. | |
| 7,354,764 B2 * | 4/2008 | Bader | A61L 27/3804 435/325 |
| 7,534,609 B2 | 5/2009 | Merchav et al. | |
| 7,670,839 B2 | 3/2010 | Bouwstra et al. | |
| 7,678,573 B2 | 3/2010 | Merchav et al. | |
| 8,524,496 B2 | 9/2013 | Meiron et al. | |
| 8,529,888 B2 | 9/2013 | Meiron et al. | |
| 9,096,827 B2 | 8/2015 | Meiron et al. | |
| 2004/0067585 A1 | 4/2004 | Wang et al. | |
| 2005/0176143 A1 | 8/2005 | Merchav et al. | |
| 2005/0181504 A1 | 8/2005 | Merchav et al. | |
| 2008/0227203 A1 | 9/2008 | Watanabe et al. | |
| 2009/0004738 A1 | 1/2009 | Merchav et al. | |
| 2009/0035857 A1 | 2/2009 | Chesnut et al. | |
| 2009/0042295 A1 | 2/2009 | Ohya et al. | |
| 2010/0209403 A1 | 8/2010 | Meiron et al. | |
| 2011/0129447 A1 | 6/2011 | Meretzki et al. | |
| 2011/0129486 A1 | 6/2011 | Meiron | |
| 2011/0171182 A1 | 7/2011 | Abelman | |
| 2011/0212493 A1 | 9/2011 | Hirschel et al. | |
| 2011/0256108 A1 | 10/2011 | Meiron et al. | |
| 2011/0256159 A1 | 10/2011 | Meiron et al. | |
| 2011/0256160 A1 | 10/2011 | Meiron et al. | |
| 2011/0293583 A1 | 12/2011 | Aberman | |
| 2012/0122220 A1 | 5/2012 | Merchav et al. | |
| 2013/0004465 A1 | 1/2013 | Aberman | |
| 2013/0039892 A1 | 2/2013 | Aberman | |
| 2013/0174287 A1 * | 7/2013 | Higuera | B01L 3/5085 800/8 |
| 2013/0259843 A1 | 10/2013 | Duda et al. | |
| 2013/0323213 A1 | 12/2013 | Meiron et al. | |
| 2013/0337558 A1 | 12/2013 | Meiron et al. | |
| 2014/0017209 A1 | 1/2014 | Aberman et al. | |
| 2014/0030805 A1 | 1/2014 | Kasuto et al. | |
| 2014/0242039 A1 | 8/2014 | Meiron et al. | |
| 2015/0125138 A1 | 5/2015 | Karnieli et al. | |
| 2015/0216907 A1 | 8/2015 | Chajut et al. | |

FOREIGN PATENT DOCUMENTS

| | | |
|---|---|---|
| GB | 2338243 A | 12/1999 |
| JP | H0564579 | 3/1993 |
| JP | 2001-507218 | 6/2001 |
| JP | 2006-136212 | 6/2006 |
| JP | 2008-035806 | 2/2008 |
| JP | 2008-237088 | 10/2008 |
| NZ | 207037 A | 1/1988 |
| WO | WO 98/24880 | 6/1998 |
| WO | WO 01/81552 A1 | 11/2001 |
| WO | WO 2005/012504 A1 | 2/2005 |
| WO | WO 2005/044972 A2 | 5/2005 |
| WO | WO 2010/088916 A2 | 8/2010 |
| WO | WO 2011/073261 A2 | 6/2011 |
| WO | WO 2012/080473 A1 | 6/2012 |

OTHER PUBLICATIONS

Timmins et al., Three-dimensional cell culture and tissue engineering in a T-CUP (tissue culture under perfusion). Tissue Eng. Aug. 2007;13(8):2021-8.

Wang et al., Modified CelliGen-packed bed bioreactors for hybridoma cell cultures. Cytotechnology. 1992;9(1-3):41-9.

Freshney, Basic principles of cell culture. Culture of cells for tissue engineering. Chapter I. 2006;3-22.

Freshney, Culture of Animal Cells—A Manual of Basic Technique. 1983. 4, 124, 176-177, 231-238.

* cited by examiner

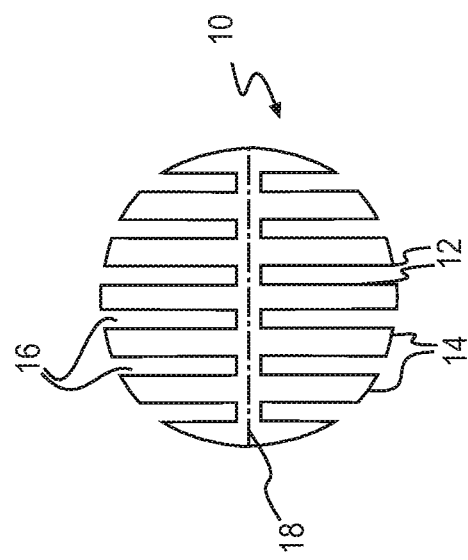
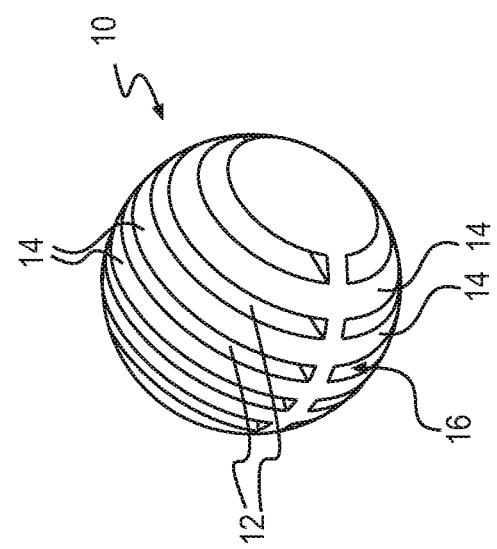
FIG. 1B
FIG. 1A

DEVICES AND METHODS FOR CULTURE OF CELLS

RELATED APPLICATIONS

This application is a national stage filing under U.S.C. §371 of PCT International Application PCT/IB2013/058184, entitled "DEVICES AND METHODS FOR CULTURE OF CELLS" with an international filing date of Aug. 31, 2013, which claims priority under 35 U.S.C. §119(e) to U.S. Provisional Application Ser. No. 61/697,445, filed on Sep. 6, 2012, which are herein incorporated by reference in their entirety.

The present disclosure relates generally to devices and methods for culturing cells.

There are several current methods of culturing eukaryotic cells. Some of these methods have been developed for culture of relatively small numbers of cells, and others have been developed for the production and harvest of proteins secreted by cells into surrounding media. Few systems, however, have been developed for commercial up-scaling of cell culture to produce large numbers of the cells.

The most common method for culturing eukaryotic cells is by expansion in two-dimensional flasks or trays, such as the NUNCLON™ A CELL FACTORY, which includes stacks of cell culture flasks. This method has several shortcomings, including the inability to continuously monitor and control environmental parameters such as DO, pH, and feed ingredients/remove waste products; low efficiency in terms of surface area to volume ratios; the need for large-volume incubators; the need for labor-intensive manipulation of culture flasks; and long time periods for seeding and culture, which can be costly and detrimental to cell viability.

In addition, cells can be cultured in three-dimensional matrices. Such matrices can include porous, non-woven/woven fiber and sponge-like materials that can be placed in a packed bed inside a bioreactor. These carriers are used primarily for the production and collection of secreted proteins, while the cells remain attached to the matrix, rather than for the culture of cells that are ultimately removed and used as therapeutic agents. Examples of such carriers are FIBRA-CELL® DISKS (New-Brunswick), and porous ceramic carriers. See Wang, G., W. Zhang, et al., "Modified CelliGen-packed bed bioreactors for hybridoma cell cultures." *Cytotechnology* 9(1-3): 41-9 (1992); and Timmins, N. E., A. Scherberich, et al., "Three-dimensional cell culture and tissue engineering in a T-CUP (tissue culture under perfusion)." *Tissue Eng* 13(8): 2021-8 (2007).

Culture in three-dimensional matrices, however, can have some drawbacks. For example, it may be relatively difficult to remove cells from the matrices, and the removal processes can damage cells. Production using such devices may be difficult because the damaged cells may not readily reattach to culture system surfaces. Differences in the type and properties of materials used in matrices and flasks can also cause variation in cell interactions.

Finally, cells may be cultured in a bioreactor using non-porous micro-carriers in suspension or in a fluidized bed. This method allows cell growth in a monolayer on the surface of micro-carriers. Using this method, however, requires separation of carriers from media by sedimentation or filtration, which are not straightforward processes and may not result in high cell-recovery rates. Furthermore, micro-carriers have deviations in surfaces on a cellular scale, which results in a culture environment that is different from two-dimensional culture systems.

The present disclosure provides devices and methods for two-dimensional culture of eukaryotic cells.

According to various embodiments, a device for cell-culture is provided. The device may comprise a three-dimensional body comprising multiple two-dimensional surfaces extending inwardly from a periphery of the three-dimensional body towards an interior of the three-dimensional body, wherein the multiple two-dimensional surfaces are configured to support monolayer growth of eukaryotic cells over at least a majority of or all of the surface area of the multiple two-dimensional surfaces, and wherein the three-dimensional body has a maximum dimension ranging from about 1 mm to about 50 mm. In contrast to conventional methods for two-dimensional culture of cells (where the cells are grown in a container that provides the two-dimensional surface), the devices described herein are introduced into a vessel containing cell growth media. For example, the devices described herein can form part of a system for cell culture as described below. Thus, in some embodiments, the devices are immersed within culture medium inside a suitable container. In providing for two-dimensional growth of cells in monolayers, the devices described herein enable controlled growth conditions to yield cells having the characteristics associated with cells grown in a two-dimensional environment.

According to various embodiments, a system for cell culture is provided. The system can comprise a container and a group of three-dimensional bodies. Each three-dimensional body can comprise multiple two-dimensional surfaces extending inwardly from a periphery of the three-dimensional body towards an interior of each three-dimensional body, wherein the multiple two-dimensional surfaces are configured to support monolayer growth of eukaryotic cells over at least a majority of or all of the surface area of the multiple two-dimensional surfaces, and wherein the three-dimensional body has a maximum dimension ranging from about 1 mm to about 50 mm.

According to various embodiments, a method for culturing cells is provided. The method can comprise selecting a group of eukaryotic cells and contacting the eukaryotic cells with at least one three-dimensional body, the at least one three-dimensional body having multiple two-dimensional surfaces extending inwardly from a periphery of the three-dimensional body towards an interior of the at least one three-dimensional body, wherein the multiple two-dimensional surfaces are configured to support monolayer growth of eukaryotic cells over at least a majority of or all of the surface area of the multiple two-dimensional surfaces, and wherein the three-dimensional body has a maximum dimension ranging from about 1 mm to about 50 mm.

According to certain embodiments, a cell-culture device is provided. The device can comprise a three-dimensional body comprising multiple two-dimensional surfaces extending inwardly from a periphery of the three-dimensional body towards an interior of the three-dimensional body, wherein the multiple two-dimensional surfaces are configured to support monolayer growth of eukaryotic cells over at least a majority of or all of the surface area of the multiple two-dimensional surfaces, and wherein the three-dimensional body has a surface area to volume ratio between about 3 $cm^2/cm^3$ and about 1,000 $cm^2/cm^3$.

According to various embodiments, a cell-culture device is provided. The device can comprise a three-dimensional body comprising a sheet of material formed into a substantially spiral configuration. The sheet of material can comprise at least two two-dimensional surfaces, wherein the two-dimensional surfaces may be configured to support monolayer growth of eukaryotic cells over at least a majority of or all of the surface area of the multiple two-dimensional surfaces, and wherein the three-dimensional body has a surface area to volume ratio between about 3 $cm^2/cm^3$ and about 1,000 $cm^2/cm^3$.

DESCRIPTION OF THE DRAWINGS

FIG. 1A is a perspective view of a device for two-dimensional cell culture, according to certain embodiments.

FIG. 1B is a cross-sectional view of the device of FIG. 1A.

DESCRIPTION OF ILLUSTRATIVE EMBODIMENTS

Figure 2A:
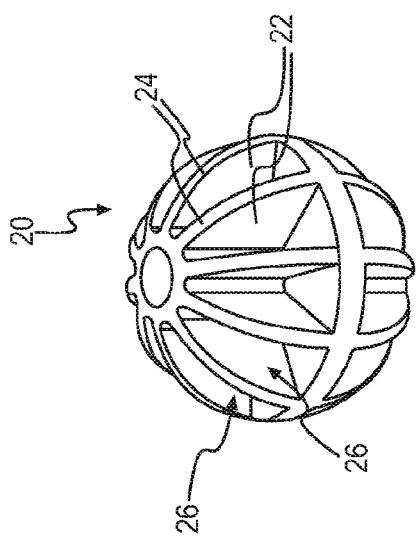
FIG. 2A is a perspective view of a device for two-dimensional cell culture, according to certain embodiments.

Reference will now be made in detail to certain exemplary embodiments according to the present disclosure, certain examples of which are illustrated in the accompanying drawings. Wherever possible, the same reference numbers will be used throughout the drawings to refer to the same or like parts.

In this application, the use of the singular includes the plural unless specifically stated otherwise. Also in this application, the use of "or" means "and/or" unless stated otherwise. Furthermore, the use of the term "including," as well as other forms, such as "includes" and "included," are not limiting. Any range described herein will be understood to include the endpoints and all values between the end points.

The devices of the present disclosure allow two-dimensional growth of eukaryotic cells. "Two dimensional growth" will be understood to include growth of eukaryotic cells along a surface wherein the majority of cell growth is in a monolayer. A "majority of cell growth in a monolayer" will be understood to include cell growth of at least 50%, at least 60%, at least 70%, at least 80%, at least 90%, at least 95%, or at least 99% of the cells in a monolayer. "Two dimensional growth" can include growth along planar (i.e., flat surfaces) and/or growth along surfaces having some degree of curvature, as described in more detail below. Thus, a "two-dimensional surface" will be understood to include a surface that is planar and/or a surface that has some curvature. In addition, as used herein the phrase "three-dimensional growth" refers to growth under conditions that are compatible with cell growth on a scaffold that allows cell-to-cell contact in three dimensions.

In allowing for two-dimensional growth, the devices of the present disclosure provide for high surface area to volume ratios, thereby allowing growth of high quantities of cells in low volumes, as compared to two-dimensional growth in flasks. Furthermore, the devices of the present disclosure can be configured to facilitate removal of cells after growth and/or transfer of cells to other environments for storage, commercial use (e.g., as therapeutic agents), or for growth of additional cells. Furthermore, the devices described herein can be configured to allow high-quality cell growth that is at least as good as that achieved using standard cell culture systems in terms of cell viability, attachability, and/or maintenance or control of other cell properties.

The devices of the present disclosure can be used to culture a variety of different eukaryotic cell types. The devices are suitable for growth of stem cells, anchorage dependent cells, mesenchymal cells, and adherent cells. As used herein the phrase "adherent cells" refers to cells that are anchorage dependent, i.e., require attachment to a surface in order to grow in vitro. Suitable adherent cells can include mesenchymal stromal cells, which are a heterogeneous population of cells obtained from, e.g., bone marrow, adipose tissue, placenta, and blood, and which may or may not be capable of differentiating into different types of cells (e.g. reticular endothelial cells, fibroblasts, adipocytes, osteogenic precursor cells) depending upon influences from various bioactive factors.

Efficient growth of various types of adherent cells can be highly dependent upon the environment or interactions experienced by the cells during growth. For example, adherent cells may be inadvertently brought into contact with other adherent cells. If one monolayer of cells inadvertently contacts another monolayer of cells, the two monolayers may adhere to each other. Such interaction between monolayers of different devices may result in attachment of devices to each other. The interaction may be mediated by extracellular matrix secreted by the cells. Because the devices described herein can limit such unwanted cell-to-cell interactions, clumping or aggregation can be generally limited. In addition, the present devices can provide efficient delivery of nutrients, medium, and gases through culture to provide a stable environment for growing monolayers of adherent cells and efficient harvesting of the cells. The devices may also promote more consistent growth of cells by limiting sub-populations of cells that grow under three-dimensional conditions as compared to two-dimensional conditions.

In one aspect, the devices described herein can be configured to limit contact between surfaces configured for cellular growth. As such, devices can be generally circular, rounded, or arcuate to generally minimize contact between surfaces of adjacent devices. Individual devices can be designed to contact adjacent devices over a relatively small area. Such limited inter-device contact can provide growing surfaces that subject growing cells to relatively small interactions with other cells growing on other devices. Multiple devices in a single incubation vessel can thus provide a more efficient, controlled, and stable growth environment for adherent cells.

In some embodiments, the devices described herein can be generally circular in cross section. For example, the outer shape of the devices can be spherical, cylindrical, and other generally rounded volumes. Such devices can provide contact areas of less than about 10% relative to the total outer surface area of the device. In other embodiments, a contact area can be less than about 5%, 2%, or 1% of the total surface area. Other shapes could also be used if contact between adjacent devices can be sufficiently minimized.

The methods of cell growth described herein may also be configured for use with the devices described herein. Vessels configured to generally resist cellular attachment can be used with these devices. For example, vessels formed from or coated with glass or plastics known to limit cellular adhesion can be used. Such vessels can encourage suitable growth of monolayers of adherent cells on the devices described herein. Such vessels may also limit possible unwanted cellular interactions, which may result in inadvertent cell-to-cell adhesions as described above.

According to various embodiments, devices for cell-culture are provided. The devices can comprise a three-dimensional body comprising multiple two-dimensional surfaces extending inwardly from a periphery of the three-dimensional body towards an interior of the three-dimensional body, wherein the multiple two-dimensional surfaces are configured to support monolayer growth of eukaryotic cells over at least a majority of or all of the surface area of the multiple two-dimensional surfaces. In some embodiments, the multiple two-dimensional surfaces may or may not support monolayer growth of eukaryotic cells over at least a majority of or all of the surface area of the multiple two-dimensional surfaces. "Multiple" two-dimensional surfaces means "more than one" two-dimensional surface and includes at least two, at least three, at least four, at least five, at least six, at least seven, at least eight, at least nine, or at least ten two-dimensional surfaces. More than ten two-dimensional surfaces are also contemplated, such as, for example, 50, 100, 500, or more surfaces. A "majority of the surface area" is understood to include at least 50%, at least 60%, at least 70%, at least 80%, at least 90%, at least 95%, or at least 99% of the surface area. In various embodiments, the devices have a maximum dimension that is less than about 50 mm and/or a surface area to volume ratio between about 3 $cm^2/cm^3$ and about 1,000 $cm^2/cm^3$. "Maximum dimension" is understood to include the largest outer height, width, length, space diagonal, vertex distance, transverse diameter, diameter, cross-sectional span, or any other largest outer spatial dimension of the three-dimensional body.

The cell-culture devices of the present disclosure can have a number of different shapes and configurations, can be formed from any of a number of suitable materials, and can include a variety of surface treatments and/or coatings to facilitate cell growth. FIGS. 1A-8B, illustrate cell-culture devices according to various embodiments, which are described in more detail below. In addition, FIG. 9 illustrates an exemplary cell-culture system including a container and a group of cell-culture devices. It will be appreciated that the devices and systems shown in the figures and described below are exemplary, and various features from the different embodiments described herein may be combined or interchanged.

FIG. 1A is a perspective view of a device 10 for two-dimensional cell culture, according to certain embodiments; and FIG. 1B is a cross-sectional view of the device 10 of FIG. 1A. As shown, the device 10 includes multiple two-dimensional surfaces 12 extending from an exterior of the device 10 towards an interior of the device 10. As shown, the surfaces are formed by a group of ribs 14 that are spaced apart to form openings 16, which may be sized to allow flow of cells and culture media during use. Device 10 can also include one or more lateral planes extending from a central axis of device 10 and extending generally perpendicular to ribs 14.

In some embodiments, an outer diameter of device 10 can range from about 1 mm to about 50 mm. In other embodiments, the outer diameter can range from about 2 mm to about 20 mm and about 4 mm to about 10 mm. Depending upon the overall size of device 10, ribs 14 and openings 16 can be variously sized. For example, ribs 14 can range in thickness from about 0.1 mm to about 2 mm and from about 0.2 mm to about 1 mm. In particular, ribs 14 can be about 0.5 mm, about 0.6 mm, or about 0.7 mm in thickness. Openings 16 can range in width from about 0.01 mm to about 1 mm and from about 0.1 mm to about 0.5 mm. In particular, openings 16 can be about 0.3 mm, about 0.4 mm, or about 0.5 mm in width.

Figure 2B:
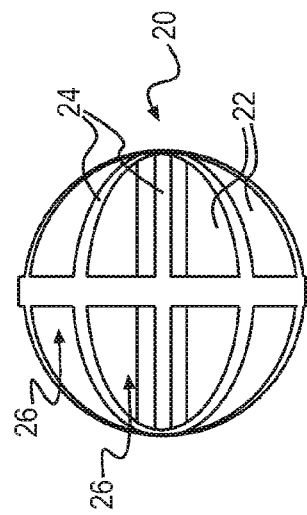
FIG. 2B is a side perspective view of the device of FIG. 2A.
Figure 2C:
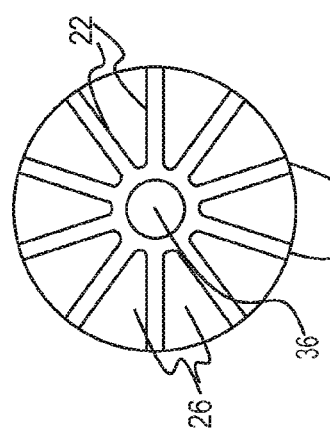
FIG. 2C is a top view of the device of FIG. 2A.
Figure 2D:
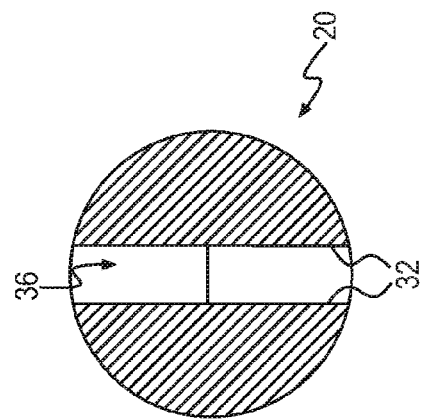
FIG. 2D is a cross-sectional view of the device of FIG. 2A.

In the embodiment shown in FIGS. 1A-1B, the ribs 14 are substantially flat and extend parallel to one another from the device's center to the device's periphery. The ribs, however, can include a variety of configurations. For example, FIGS. 2A-2D illustrate a device 20 having multiple two-dimensional surfaces 22 formed by ribs 24 in a different configuration. FIG. 2A is a perspective view of the device 20 for two-dimensional cell culture, according to certain embodiments; FIG. 2B is a side perspective view of the device of FIG. 2A; FIG. 2C is a top view of the device of FIG. 2A; and FIG. 2D is a cross-sectional view of the device of FIG. 2A. The device 20 of FIGS. 2A-2D is similar to the device 10 of FIGS. 1A-1B, but the ribs 24 of device 20 are shaped to form openings 26 that are spaced around the circumference of the device 20. Openings 26 can be generally wedge shaped. Ribs 24 can extend generally radially from a central axis of device 20 to a peripheral surface of device 20. Device 20 can also include one or more lateral planes extending from the central axis of device 20 and extending generally perpendicular to ribs 24. Further, the device 20 includes an opening 36 extending through the device's center and forming additional surfaces 32, which can support monolayer growth of eukaryotic cells.

As described above for device 10, the dimensions of device 20 can be variously sized. For example, an outer diameter of device 20 can range from about 1 mm to about 50 mm. In other embodiments, the outer diameter can range from about 2 mm to about 20 mm and about 4 mm to about 10 mm. Depending upon the overall size of device 20, ribs 24 and openings 26 can be variously sized. For example, ribs 24 can range in thickness from about 0.1 mm to about 2 mm and from about 0.2 mm to about 1 mm. In particular, ribs 24 can be about 0.5 mm, about 0.6 mm, or about 0.7 mm in thickness. As shown in FIGS. 2A-2C, openings 26 can range in width from a minimum width generally located about a central axis extending through device 20 or opening 36, to a maximum width generally located about a periphery of device 20. A minimum width of openings 26 can range from about 0.01 mm to about 1 mm and from about 0.1 mm to about 0.5 mm. Specifically, the minimum width of openings 26 can be about 0.3 mm, about 0.4 mm, or about 0.5 mm. In addition, opening 36 can range in diameter from about 0.1 mm to about 5 mm and from about 0.5 mm to about 2 mm. More particularly, opening 36 can have a diameter of about 0.8 mm, about 1 mm, or about 1.2 mm.

As shown, the devices 10, 20 are substantially spherical and have a diameter 18 that forms the devices' largest dimension. The devices described herein can have a variety of different shapes and configurations, as long as the devices provide two-dimensional surfaces for attachment and monolayer growth over at least a majority of or all of the surface area of the multiple two-dimensional surfaces 12, 22.

Figure 3A:
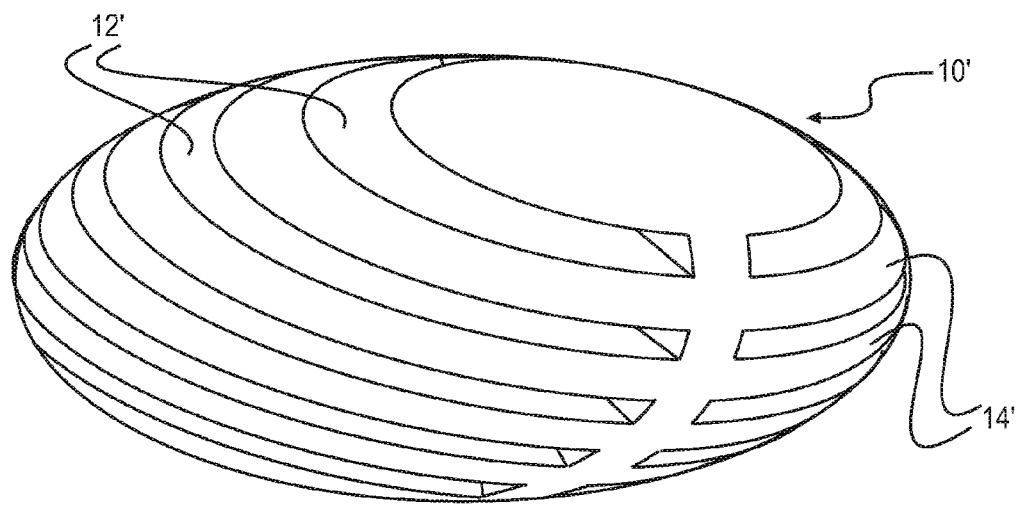
FIG. 3A is a perspective view of a device for two-dimensional cell culture, according to certain embodiments.
Figure 3B:
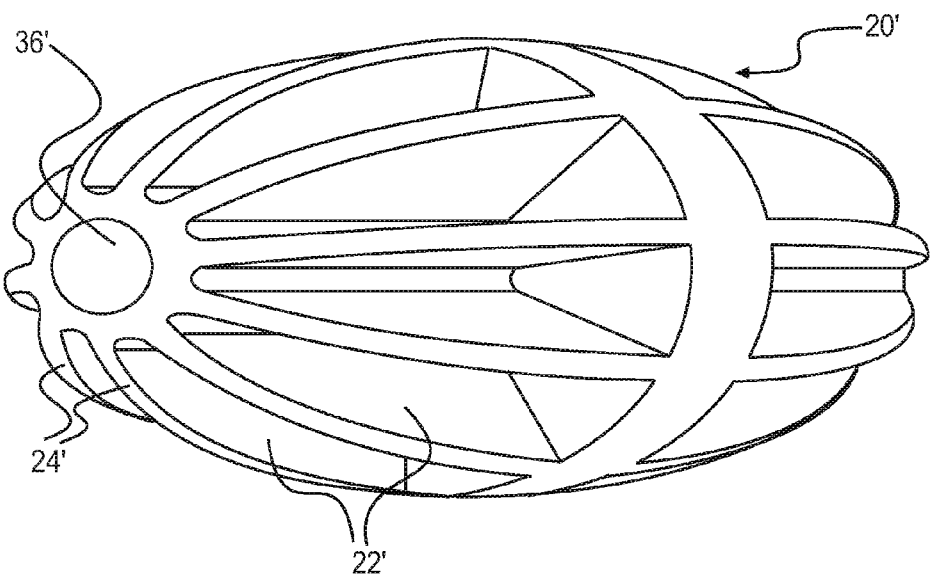
FIG. 3B is a perspective view of a device for two-dimensional cell culture, according to certain embodiments.

The cell-culture devices of the present disclosure can include a variety of shapes and configurations. For example, although the devices described above with respect to FIGS. 1A-2D are substantially spherical, other suitable shapes by be used. For example, FIGS. 3A-3B are perspective views of devices 10', 20' for two-dimensional cell culture. The devices 10', 20' are similar to the devices 10, 20 of FIGS. 1A-2D except that the devices 10', 20' have substantially ovoid shapes, but similarly provide multiple two dimensional surfaces 12,' 22' formed by ribs 14', 24' or openings 36'. Further, other suitable shapes may be used, including other polyhedral and/or irregular polyhedral shapes.

Figure 4B:
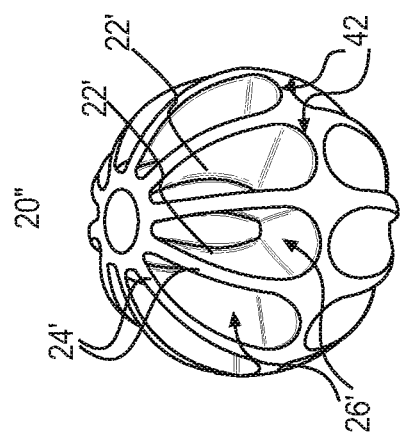
FIG. 4B is a perspective view of a device for two-dimensional cell culture, according to certain embodiments.
Figure 4A:
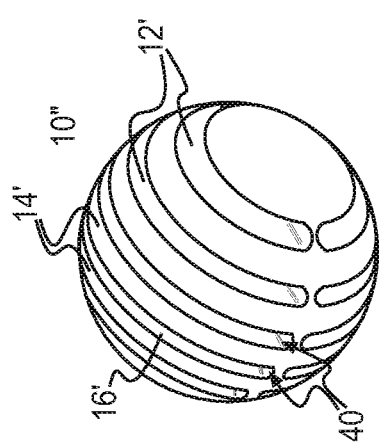
FIG. 4A is a perspective view of a device for two-dimensional cell culture, according to certain embodiments.

As discussed above, the devices of the present disclosure can include multiple two-dimensional surfaces configured to support monolayer growth of eukaryotic cells over at least a majority of or all of the surface area of the multiple two-dimensional surfaces. In certain embodiments, the multiple two-dimensional surfaces are configured to support monolayer growth over substantially all of their surface area. For example, FIGS. 4A-4B are perspective views of devices for two-dimensional cell culture, according to certain embodiments, which are configured to support monolayer growth over substantially all of their surface area. The devices 10", 20" of FIGS. 4A-4B are similar to other devices described above and comprise surfaces 12', 22' formed by ribs 14', 24'. However, the devices 10", 20" have openings 16', 26' with surfaces 12', 22' that form smooth curves along their entire areas, thereby eliminating or reducing areas of sharp curvature where three-dimensional growth may occur. For example, as shown, the devices 10", 20" have smoothly curved lower surfaces 40, 42, as opposed to sharper curves, as illustrated with respect to the devices of FIGS. 1A-2D.

Figure 5:
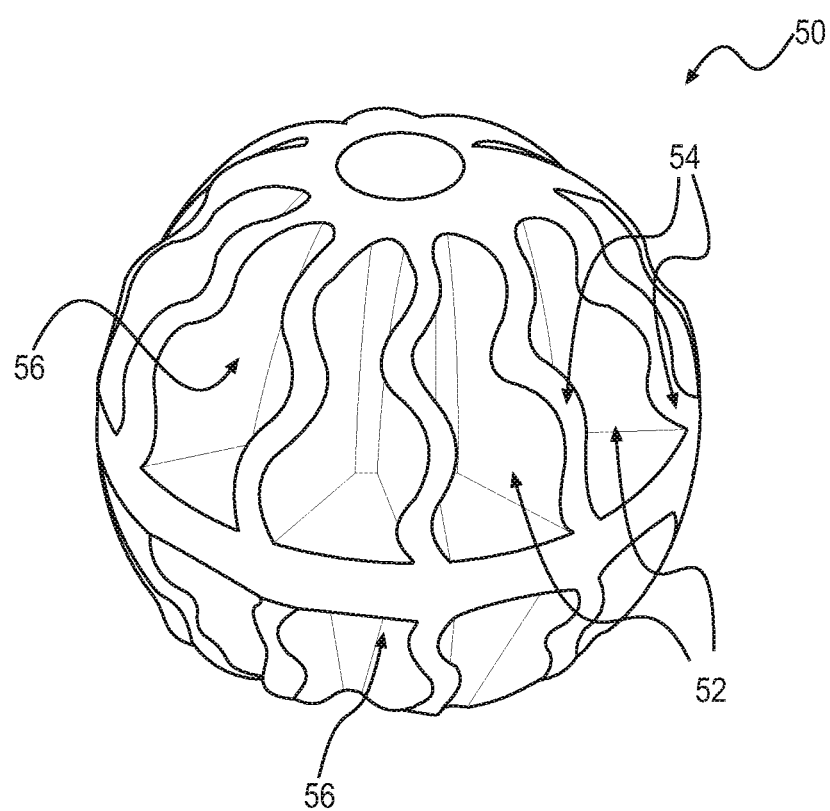
FIG. 5 is a perspective view of a device for two-dimensional cell culture, according to certain embodiments.

In various embodiments, the specific curvature and configuration of the multiple two-dimensional surfaces can be modified, e.g., to provide higher surface areas and/or to control cell growth. For example, FIG. 5 is a perspective view of a device 50 for two-dimensional cell culture, according to certain embodiments. The device 50 includes ribs 54 that extend from a periphery of the device 50 towards an interior of the device to form openings 56 and multiple two-dimensional surfaces 52 for monolayer growth. As shown, the ribs 54 and surfaces 52 are curved. The curved shape of the surfaces 52 can further increase the surface area of the multiple two-dimensional surfaces 52, as compared to flat surfaces, thereby providing additional area for cell attachment and monolayer growth.

Figure 6:
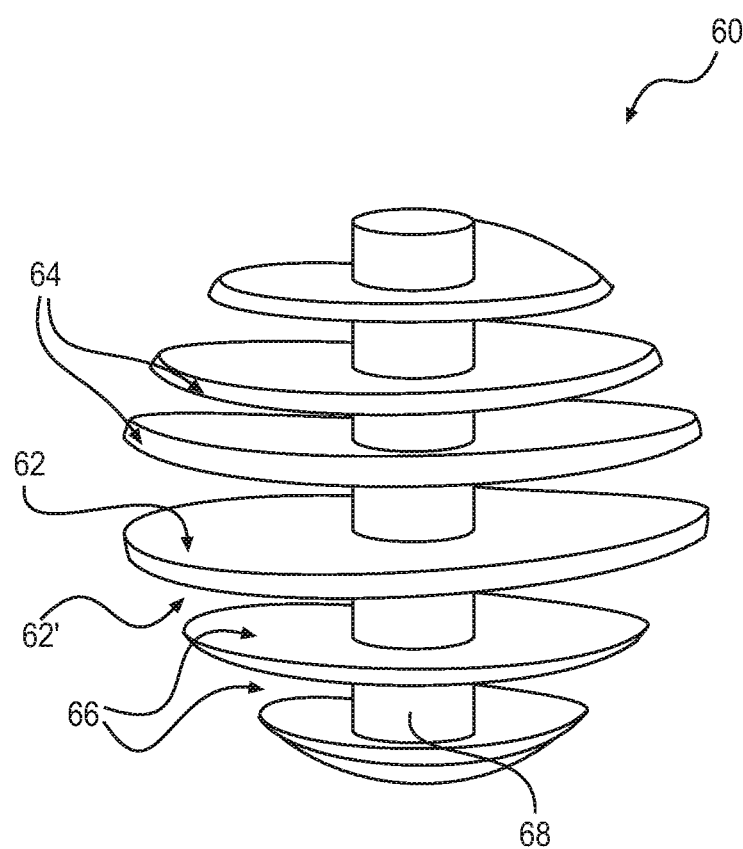
FIG. 6 is a perspective view of a device for two-dimensional cell culture, according to certain embodiments.

FIG. 6 is a perspective view of a device 60 for two-dimensional cell culture, according to certain embodiments. As shown, the device 60 includes ribs 64 extending from an interior of the device 60 towards a periphery of the device 60. The ribs 64, can include a spiral configuration that extends at least partially along a diameter of the device 60 to form at least two two-dimensional surfaces 62, 62' for two-dimensional growth of eukaryotic cells. As shown, the ribs extend from a core portion 68 towards the periphery of the device 60.

Figure 7:
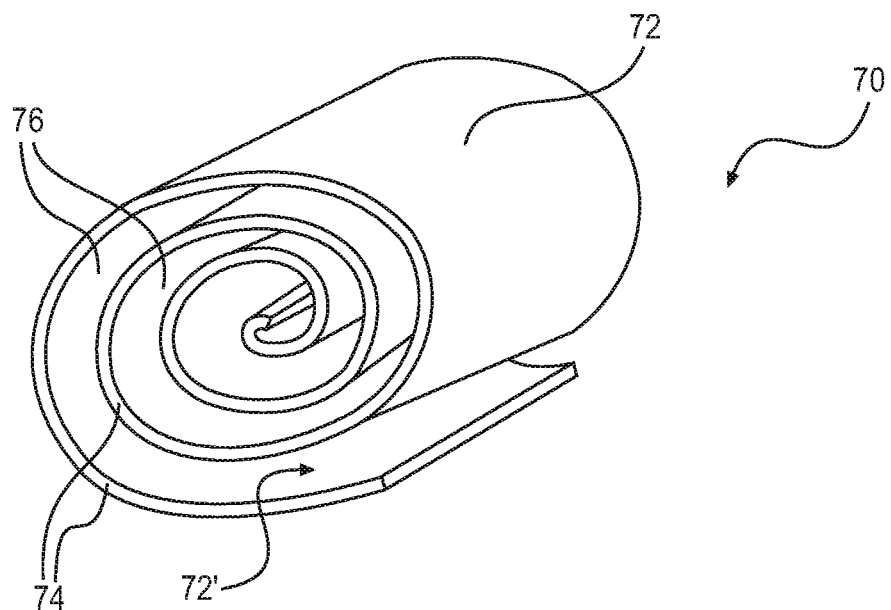
FIG. 7 is a perspective view of a device for two-dimensional cell culture, according to certain embodiments.

In each of the embodiments described above, the multiple two-dimensional surfaces extend from an interior core. According to other embodiments, however, the surfaces may extend inwardly within being directed towards a central core. For example, FIG. 7 illustrates another device 70, according to some embodiments. The device 70 includes at least one sheet of material in the form of a substantially spiral-shaped wall 74 with an opening 76, and having at least a first surface 72 and a second surface 72' configured to allow two-dimensional growth of eukaryotic cells. It will be appreciated, however, that other shapes can be used, and the device 70 need not be a continuous spiral, and may include other configurations.

Figure 8B:
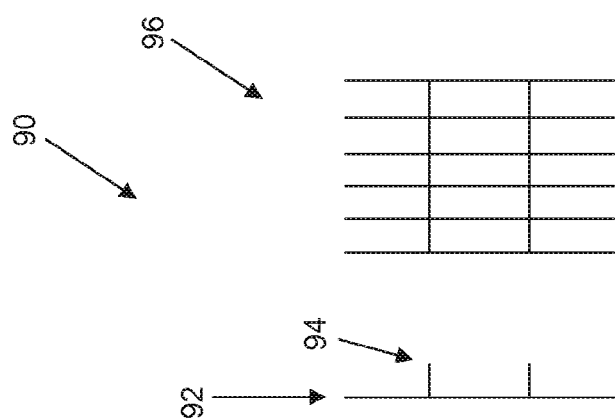
FIG. 8B is a cross-sectional view of the device of FIG. 8A.
Figure 8A:
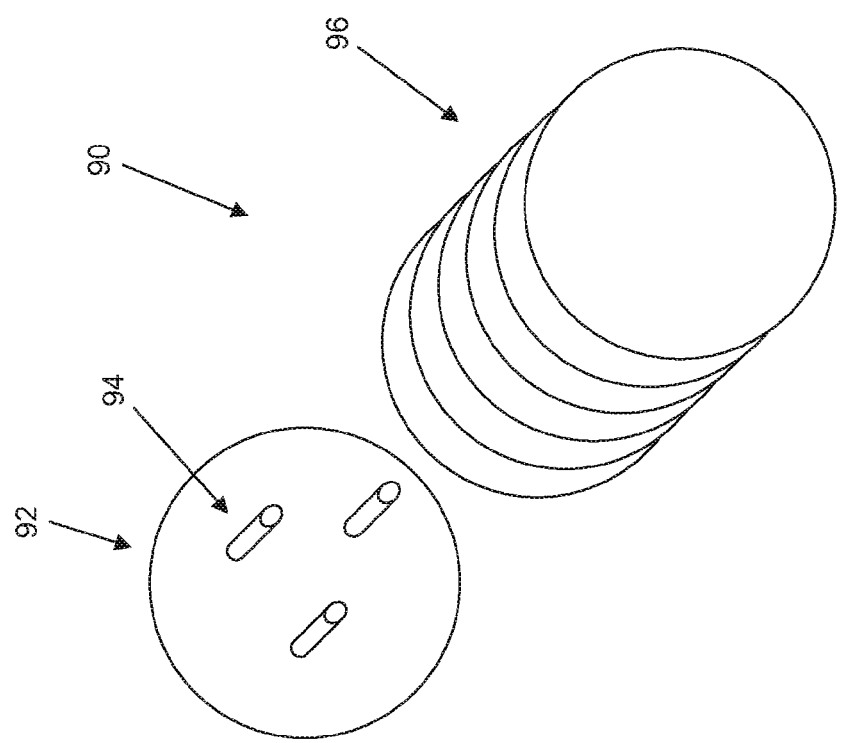
FIG. 8A is a perspective view of a device for two-dimensional cell culture, according to certain embodiments.
Figure 9:
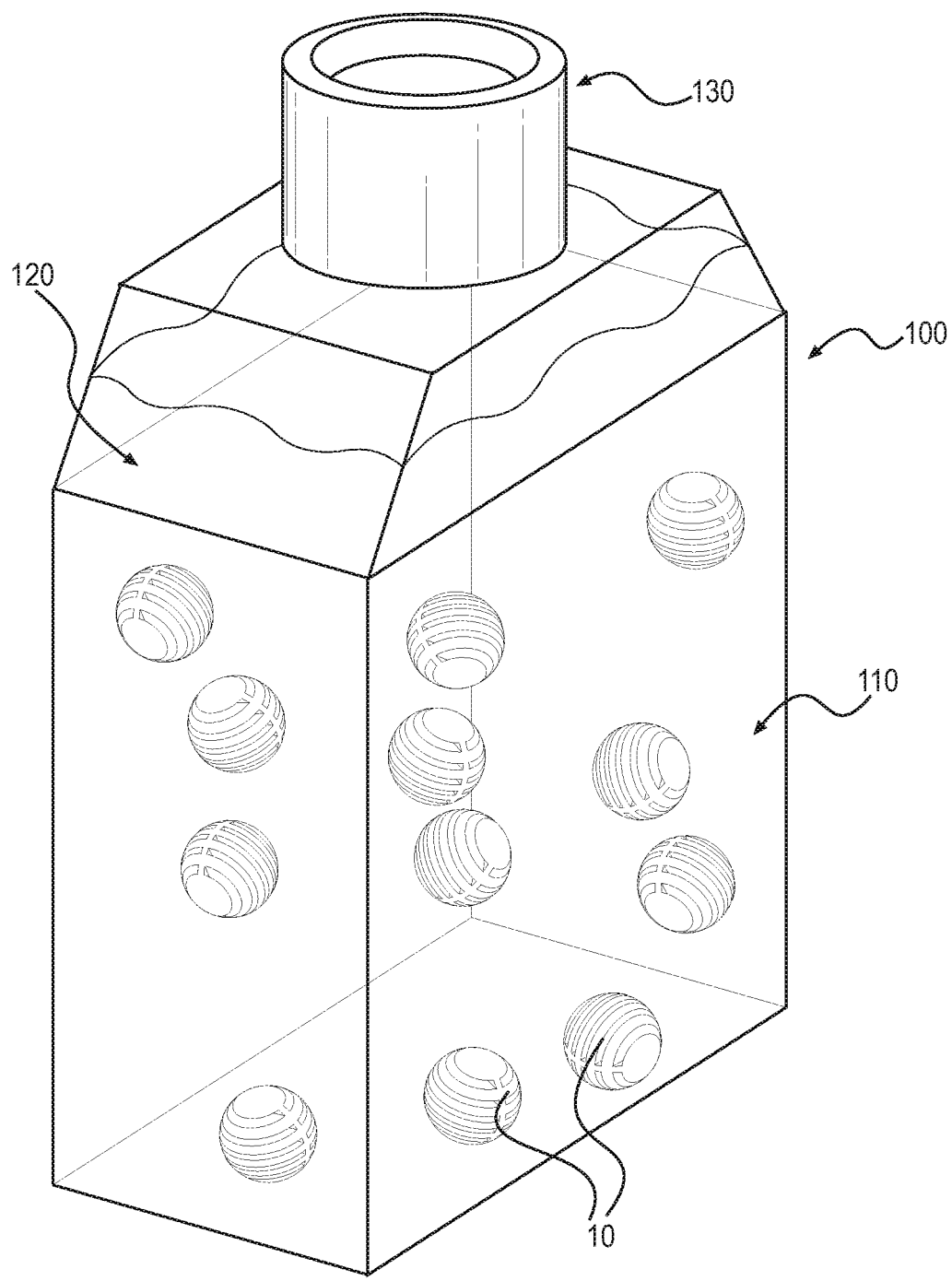
FIG. 9 is a perspective view of a system for two-dimensional cell culture, according to certain embodiments.

It is also contemplated that a device 90 can include one or more detachable components, as shown in FIGS. 8A, 8B. For example, device 90 can include one or more detachable discs 92. Each disc 92 can include one or more connectors 94 configured to couple to another structural element of device 90. As such, a plurality of discs 92 can be coupled together to form an assembly 96. Assembly 96 can include any number of discs 92 or connectors of various shapes or sizes, including the embodiments shown above in FIGS. 1-7.

Disc 92 can be any shape and can include a female coupling (not shown), configured to couple to connector 94. Coupling between disc 92 and connector 94 can be permanent or detachable. In other embodiments, a plurality discs 92 can be coupled to a single connector 94 configured to receive the plurality of discs 92 and maintain a suitable distance between the plurality of discs 92.

The various cell culture devices described above can be formed into a variety of shapes. While many embodiments depict the devices as rounded, the devices may also be cubic, rectangular, or a combination of linear and arcuate forms. Moreover, additional stabilizing, connective, or other structural features may be used with these devices. For example, a threadlike member may couple multiple devices together, an adhesive member may couple a device to a wall of an incubation vessel, or a flotation member may allow a device to remain buoyant in a fluid to limit cells inadvertently coming into contact with other surfaces. Such members can enhance handling using manual or automated techniques.

For example, magnetic material may be incorporated into the devices to aid collection and processing steps. The devices may also be configured for continuous exposure to an incubation fluid or for intermittent exposure to the fluid.

The cell culture devices described herein can be produced using a variety of different suitable materials. Generally, the devices can be produced by using materials that have a wide range of attributes selected to allow cell culture for pharmaceutical purposes. In various embodiments, the materials can be USP class 6 (US Pharmacopeial Convention Class VI) approved, may withstand high temperatures and are autoclavable, are amenable to plasma or corona treatment to improve cell attachment, can withstand a wide range of pHs, do not leach harmful substances during the cell growth process, and/or can be exposed to enzymatic and physical stresses to removes cells without being degraded or leaving unwanted residues in the product. In addition, the material used to produce any of the devices describe herein can be solid or have a hollow or porous interior. Further, the devices described herein can be produced from a single piece of material, or from two or more pieces that are attached to one another (e.g., by chemical or physical bonding). The material may be rigid or flexible as required by application.

The material used to produce any of the cell culture devices described herein can include metals (e.g. titanium), metal oxides (e.g., titanium oxide films), glass, borosilicate, carbon fibers, ceramics, biodegradable materials (e.g. collagen, gelatin, PEG, hydrogels), and or polymers. Suitable polymers may include polyamides, such as GRILAMID® TR 55 (EMS-grivory); polycarbonates such as LEXAN® (Sabic) and Macrolon® (Bayer); polysulfones such as RADEL® PPSU (Solvay) and UDEL® PSU (Solvay); polyesters such as TRITAN® (Polyone) and PBT® HX312C; polyacetals such as CELON® (Ticana), and polyvinyl chloride.

In some embodiments, at least part of the devices may be formed using a polystyrene polymer. The polystyrene may be further modified using corona discharge, gas-plasma (roller bottles and culture tubes), or other similar processes. These processes can generate highly energetic oxygen ions which graft onto the surface polystyrene chains so that the surface becomes hydrophilic and negatively charged when medium is added (Hudis, 1.974; Amstein and Hartman, 1975; Ramsey et. al, 1984). Furthermore, any of the devices may be produced at least in part from combinations of materials. Materials of the devices can be further coated or treated to support cell attachment. Such coating and/or pretreatment may include use of collagen I, collagen IV, gelatin, poly-d-lysine, fibronectin, laminin, amine, and carboxyl.

In some embodiments, the materials used to produce the devices are selected to allow direct attachment by eukaryotic cells. The devices described herein can be produced using a variety of suitable production processes. For example, in some embodiments, the devices may be produced by injection moulding using, for example, one or more polymeric materials.

In addition, the material properties and curvature over most or all of the surface area of the two-dimensional surfaces may be selected to control certain biological properties. For example, the material may be selected to have a certain elastic modulus and curvature to produce desired biologic properties. For example, suitable elastic moduli can be between about 0.1-100 kPa.

In various embodiments, the devices have a size selected to facilitate collection (e.g., by filtration, scooping, removing media), and minimize void space between devices. For example, the three-dimensional bodies may have a maximum dimension between about 1 mm and 50 mm, between about 1 mm and 20 mm, or between about 2 mm and 10 mm. In certain embodiments, the devices are spherical and have a maximum diameter that is between about 1 mm and 50 mm, between about 1 mm and 20 mm, or between about 2 mm and 10 mm.

In certain embodiments, the devices are configured to prevent damage to or removal of cells from the two-dimensional surfaces during culture. For example, as shown in FIGS. 1A-8B, the devices can include openings 16, 26, 16', 26', and 76, and the two-dimensional surfaces are located within the openings. In various embodiments, the multiple two-dimensional surfaces are spaced from one another at a distance selected to prevent contact of objects adjacent to the three-dimensional body with cells growing on the multiple two-dimensional surfaces. Specifically, the openings 16, 26, 16', 26', or 76 may be sized such that the two-dimensional surfaces will not be contacted by adjacent devices within a culture system and/or will not be contacted by the wall of a container or culture vessel. As such, the monolayer growth of cells along the two-dimensional surfaces will not be disturbed by mechanical contact. Furthermore, the two-dimensional surfaces may be spaced far enough from one another to prevent contact between cells on adjacent surfaces.

In various embodiments, the cell culture devices of the present disclosure can be configured to provide a desired surface area to volume ratio. For example, the surface area to volume ratio of any of the cell-culture devices described herein can be between about 3 $cm^2/cm^3$ and 30 $cm^2/cm^3$, between about 5 $cm^2/cm^3$ and 20 $cm^2/cm^3$, or between about 10 $cm^2/cm^3$ and 15 $cm^2/cm^3$. In other embodiments, the surface area to volume ratio can range up to about 50, 100, 200, 500, or 1,000 $cm^2/cm^3$.

In various embodiments, the devices disclosed herein may further be coated with one or more coatings. Suitable coatings may be selected to control cell attachment or changes to cell biology. Suitable coatings may include, for example, peptides, proteins, carbohydrates, nucleic acid, lipids, polysaccharides, glycosaminoglycans, proteoglycans, hormones, extracellular matrix molecules, cell adhesion molecules, natural polymers, enzymes, antibodies, antigens, polynuceotides, growth factors, synthetic polymers, polylysine, drugs and/or other molecules or combinations or fragments of these.

Furthermore, in various embodiments, the surfaces of the devices described herein may be treated or otherwise altered. To control cell attachment and or other biologic properties. Options for treating the surfaces including chemical treatment, plasma treatment, and/or corona treatment. Further, in various embodiments, the materials may be treated to introduce functional groups into or onto the material, including groups containing hydrocarbons, oxygen, nitrogen. In addition, in various embodiments, the material may be produced or altered to have a texture to facilitate cell attachment or control other cell properties. For example, in some embodiments, the materials used to produce the cell-culture devices have a roughness on a nanometer or micrometer scale that facilitates cell attachment and/or controls other cell properties.

According to various embodiments, a system for cell culture is provided. The system can comprise a container and a group of three-dimensional bodies. The three-dimensional bodies can comprise multiple two-dimensional surfaces extending inwardly from a periphery of each three-dimensional body towards an interior of each three-dimensional body, wherein the multiple two-dimensional surfaces are configured to support monolayer growth of eukaryotic cells over at least a majority of or all of the surface area of the multiple two-dimensional surfaces.

FIG. 9 is a perspective view of a system 100 for two-dimensional cell culture, according to certain embodiments. As shown, the system 100 includes a container 110 and one or more cell culture devices 110 that may be placed within the container 100 along with media 120 and/or other materials to allow two-dimensional growth of cells on the surface of the container 110.

As shown, the container 100 includes a common cell-culture flask having an opening 130 for introduction of cells, cell culture devices 110, media, and/or other materials. In will be appreciated, however, that other containers may be selected. For example, the container may be much larger, e.g., selected to hold dozens, hundreds, thousands, hundreds of thousands, or millions of cell-culture devices. The specific size and configuration may be selected based on the amount of cells to be cultured and/or other criteria, such as the need for integrated systems to control culture conditions such as temperature, pH, surrounding gas levels, etc.

In various embodiments, the system can include a bioreactor container such as a packed bed reactor, fluidized reactor, or suspension reactor. For example, the system can include one or more of the devices to allow two-dimensional growth, which can then be placed in the container of a bioreactor. Examples of such bioreactors include, but are not limited to, a plug flow bioreactor, a continuous stirred tank bioreactor, a stationary-bed bioreactor (packed bed bioreactor) and a fluidized bed bioreactor.

An example of a suitable bioreactor is the Celligen bioreactor (New Brunswick Scientific), which is capable of expansion of adherent cells under controlled conditions (e.g. pH, temperature and oxygen levels) and with constant cell growth medium perfusion. Furthermore, the cell cultures can be monitored for concentration levels of glucose, lactate, glutamine, glutamate and ammonium. The glucose consumption rate and the lactate formation rate of the adherent cells enable one to measure cell growth rate and to determine the harvest time.

Other three-dimensional bioreactors that can be used include, but are not limited to, a continuous stirred tank bioreactor, where a culture medium is continuously fed into the bioreactor and the used medium is continuously drawn out, to maintain a time-constant steady state within the bioreactor. The stirred tank bioreactor may be used with fluidized bed (suspended carriers) or a fibrous bed basket (which is available for example at New Brunswick Scientific Co., Edison, N.J.), a stationary-bed bioreactor, an air-lift bioreactor, where air is typically fed into the bottom of a central draught tube flowing up while forming bubbles, and disengaging exhaust gas at the top of the column, a bioreactor with Polyactive foams [as described in Wendt, D. et al, Biotechnol Bioeng 84: 205-214, (2003)], a porous scaffolds in a Radial-flow perfusion bioreactor [as described in Itagawa et al., Biotechnology and Bioengineering 93(5): 947-954 (2006)], a radial flow bioreactor with scaffold or carriers, a hollow fiber bioreactor, and micro carriers. Other bioreactors, which can be used with the presently described devices and system, are described in U.S. Pat. Nos. 6,277, 151; 6,197,575; 6,139,578; 6,132,463; 5,902,741; and 5,629,186.

The present disclosure also provides methods of culturing cells using any of the devices or systems discussed herein. According to various embodiments, the method can comprise selecting a group of eukaryotic cells and contacting the eukaryotic cells with at least one three-dimensional body, the at least one three-dimensional body having multiple two-dimensional surfaces extending inwardly from a periphery of the three-dimensional body towards an interior of the at least one three-dimensional body, wherein the multiple two-dimensional surfaces are configured to support monolayer growth of eukaryotic cells over at least a majority of or all of the surface area of the multiple two-dimensional surfaces. In various embodiments, the devices have a maximum dimension that is less than about 50 mm and/or a surface area to volume ratio between about 3 $cm^2/cm^3$ and about 1,000 $cm^2/cm^3$.

In addition, it will be appreciated that various processing steps can be performed to control or enhance attachment and growth of the cells. For example, the cells may be contacted with the three-dimensional bodies by placing the cells and bodies within a container or culture vessel along with culture media. Further, the cells and/or media can be mixed or otherwise made to move by, for example, rotating the container, agitating the culture media (e.g., by stirring), and supplying fluid flow into and out of the container.

Non-limiting examples of base media useful in culturing using the devices and systems described herein include Minimum Essential Medium Eagle, ADC-1, LPM (Bovine Serum Albumin-free), F10(HAM), F12 (HAM), DCCM1, DCCM2, RPMI 1640, BGJ Medium (with and without Fitton-Jackson Modification), Basal Medium Eagle (BME—with the addition of Earle's salt base), Dulbecco's Modified Eagle Medium (DMEM-without serum), Yamane, IMEM-20, Glasgow Modification Eagle Medium (GMEM), Leibovitz L-15 Medium, McCoy's 5 A Medium, Medium M1 99 (M199E—with Earle's sale base), Medium M199 (M199H—with Hank's salt base), Minimum Essential Medium Eagle (MEM-E—with Earle's salt base), Minimum Essential Medium Eagle (MEM-H—with Hank's salt base) and Minimum Essential Medium Eagle (MEM-NAA with non essential amino acids), among numerous others, including medium 199, CMRL 1415, CMRL 1969, CMRL 1066, NCTC 135, MB75261, MAB 8713, DM 145, Williams' G, Neuman & Tytell, Higuchi, MCDB 301, MCDB 202, MCDB 501, MCDB 401, MCDB 411, MDBC 153. A preferred medium for use in the invention is DMEM. These and other useful media are available from GIBCO, Grand Island, N.Y., USA and Biological Industries, Bet HaEmek, Israel, among others. A number of these media are summarized in Methods in Enzymology, Volume LVIII, "Cell Culture", pp. 62 72, edited by William B. Jakoby and Ira H. Pastan, published by Academic Press, Inc.

The medium may be supplemented such as with serum such as fetal serum of bovine or human or other species, and optionally or alternatively, growth factors, vitamins (e.g. ascorbic acid), cytokines, salts (e.g. B-glycerophosphate), steroids (e.g. dexamethasone) and hormones e.g., growth hormone, erythropoeitin, thrombopoietin, interleukin 3, interleukin 6, interleukin 7, macrophage colony stimulating factor, c-kit ligand/stem cell factor, osteoprotegerin ligand, insulin, insulin like growth factors, epidermal growth factor, fibroblast growth factor, nerve growth factor, cilary neurotrophic factor, platelet derived growth factor, and bone morphogenetic protein at concentrations of between picogram/ml to milligram/ml levels.

After growth of cells using the devices and systems described herein, cells can be harvested in a variety of different ways. For example, cells can be harvested by washing with suitable media and/or by vibration based harvesting, as described below.

It is further recognized that additional components may be added to the culture medium. Such components may be antibiotics, antimycotics, albumin, amino acids, and other components known to the art for the culture of cells.

Example 1

The suitability of cell culture using various carriers, as described herein, was evaluated. Fresh or frozen PD051010 p.3/2 cells were cultured with full DMEM in a humidified incubator. Cells were grown with injection-moulded carriers produced from various polymeric materials or flasks, as identified below. The material, shape and configuration, surface treatments, and surface texture were varied, as described in detail below and/or indicated in the figures. The growth rate and attachment efficiency of cells using different carriers were measured, and the results are summarized below.

Figure 10:
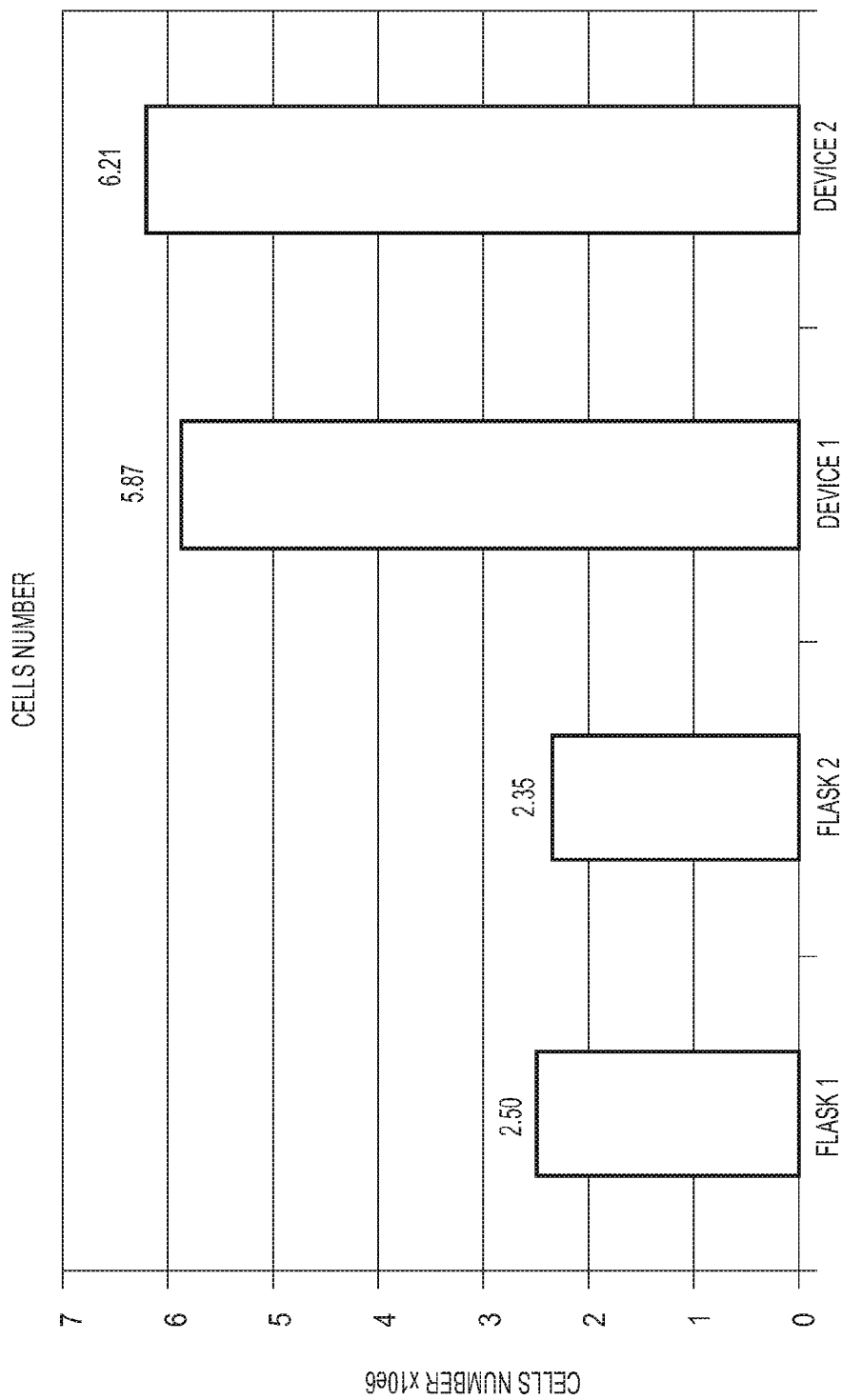
FIG. 10 is a bar graph showing results of cell culture in flasks or using the two-dimensional culture devices of the present disclosure, as described in Example 1.
Figure 11:
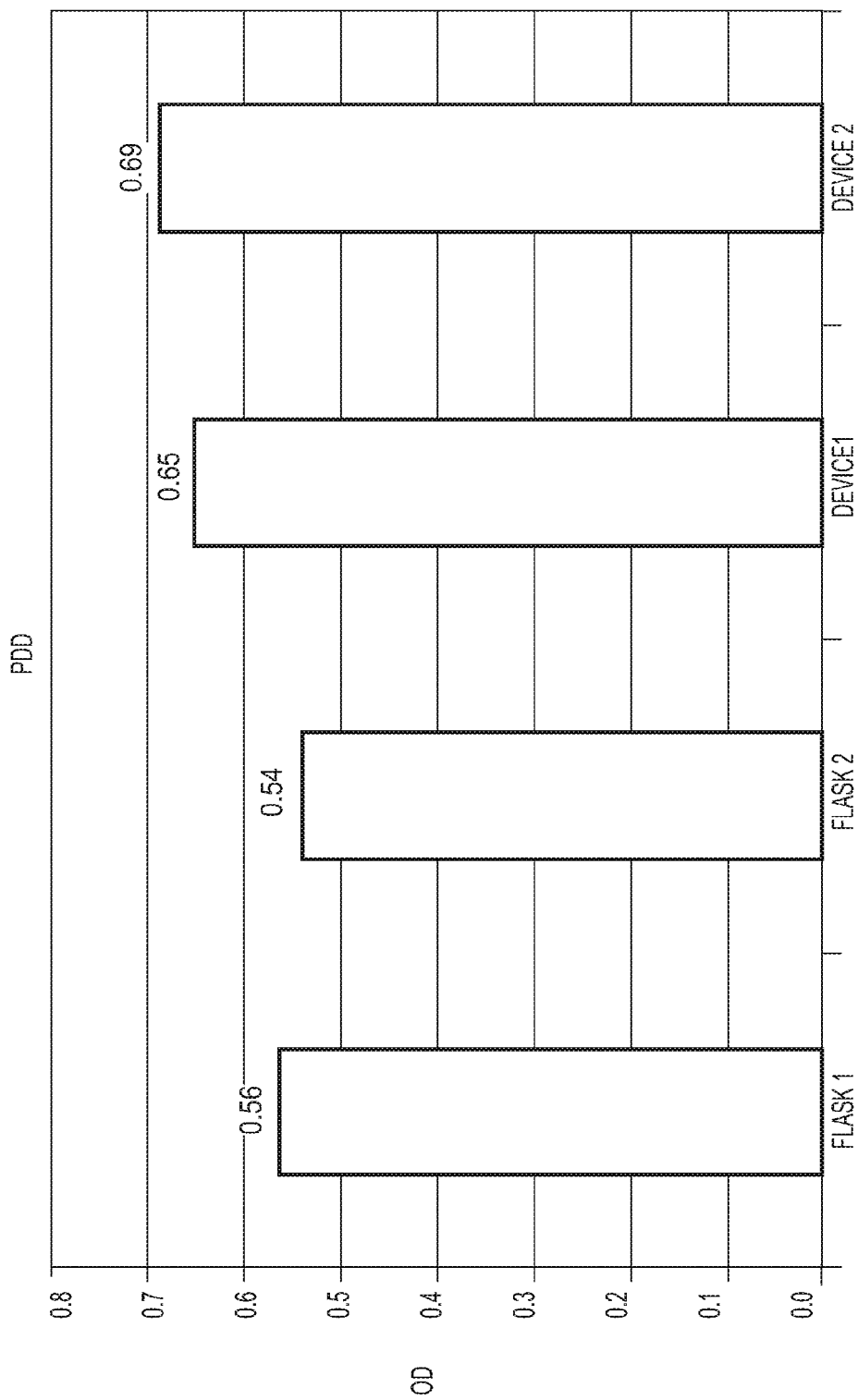
FIG. 11 is a bar graph showing the population duplication number of cells cultured in flasks or using the two-dimensional culture devices of the present disclosure, as described in Example 1.

FIG. 10 is a bar graph showing results of cell culture in 175 cm$^2$ flasks or using the two-dimensional culture devices of the present disclosure. FIG. 11 is a bar graph showing the population duplication number of cells cultured in 175 cm$^2$ flasks or using the two-dimensional culture devices of the present disclosure. The results shown in FIGS. 10-11 are based on culture of fresh PD051010 p.3/2 cells using cell-culture devices formed of injection-moulded LEXAN® with a smooth surface texture and having a configuration as shown in FIGS. 1A-1B. As shown in the figures, the amount of cells obtained and cell duplication number were similar using the cell-culture devices instead of flasks.

Figure 12:
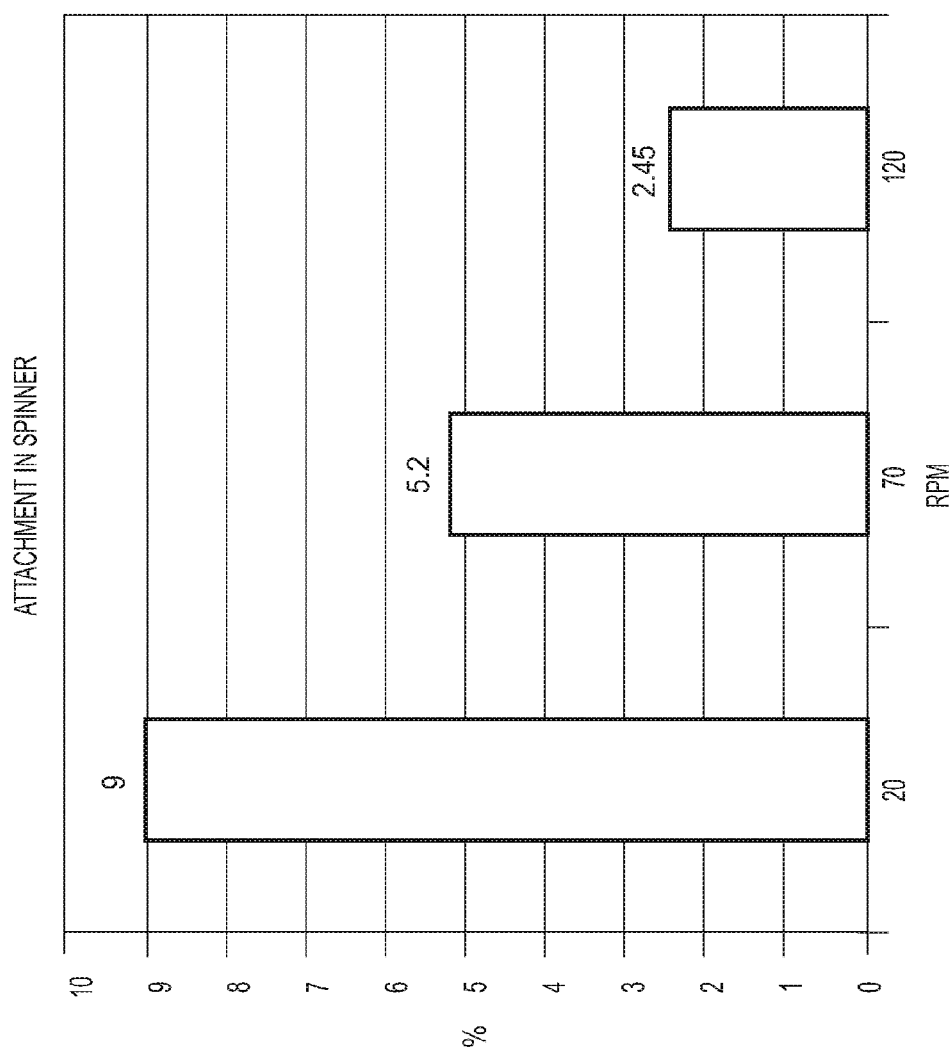
FIG. 12 is a bar graph illustrating cell attachment efficiency for cells grown using two-dimensional culture devices, at different medium mixing speeds (RPM) as described in Experiment 1.
Figure 13:
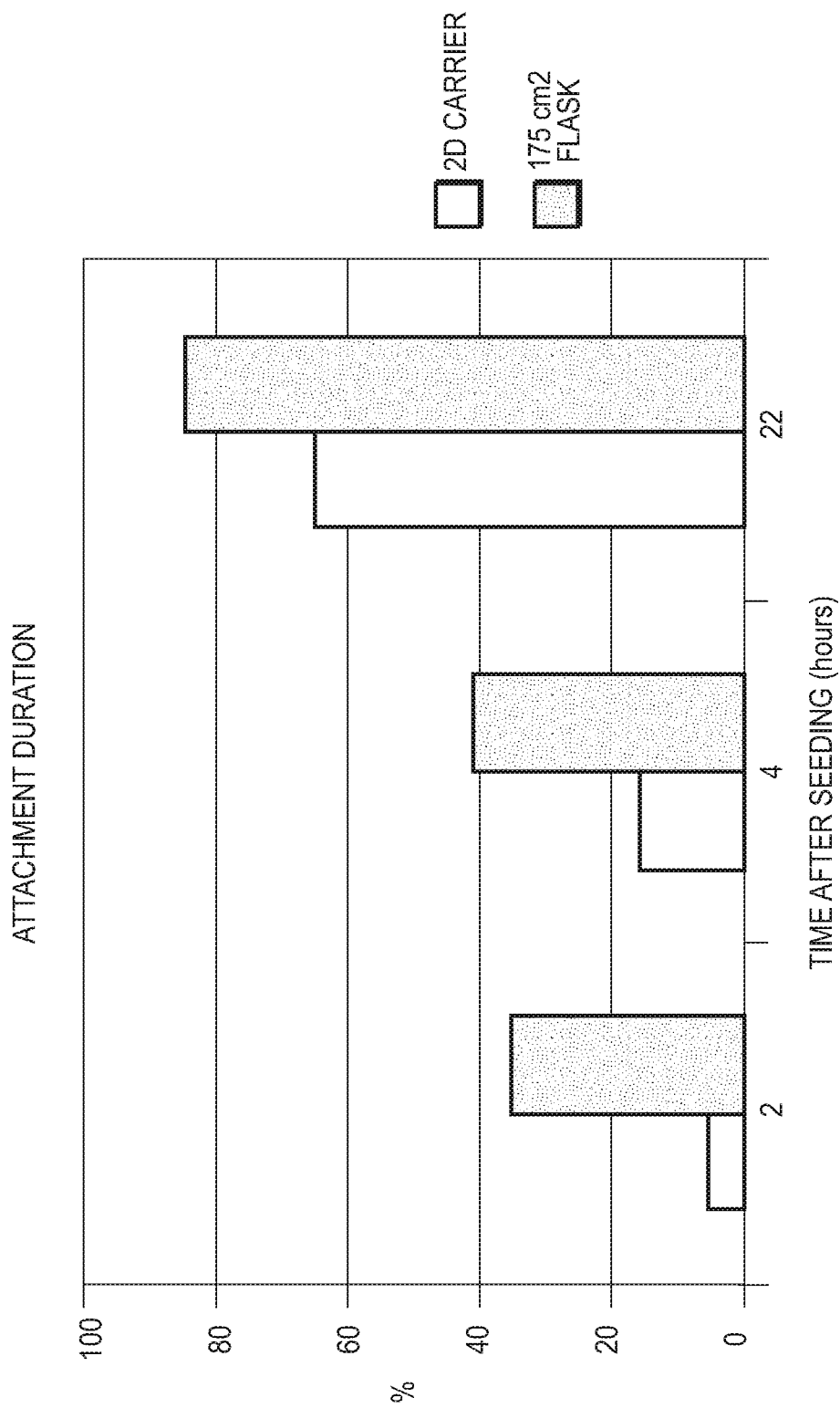
FIG. 13 is a bar graph illustrating cell attachment efficiency for cells grown using two-dimensional culture devices, as described in Experiment 1.

FIG. 12 is a bar graph illustrating cell attachment efficiency for cells grown using two-dimensional culture devices. The results shown in FIG. 12 are based on culture of frozen PD051010 p.3/2 cells using cell-culture devices formed of injection-moulded LEXAN® with a rough surface texture and having a configuration as shown in FIGS. 1A-1B. FIG. 13 is a bar graph illustrating cell attachment efficiency for cells grown using two-dimensional culture devices. The results shown in FIG. 13 are based on culture of frozen PD051010 p.3/2 cells using cell-culture devices formed of injection-moulded GRILAMID® with a rough surface texture and having a configuration as shown in FIGS. 1A-1B.

Figure 14:
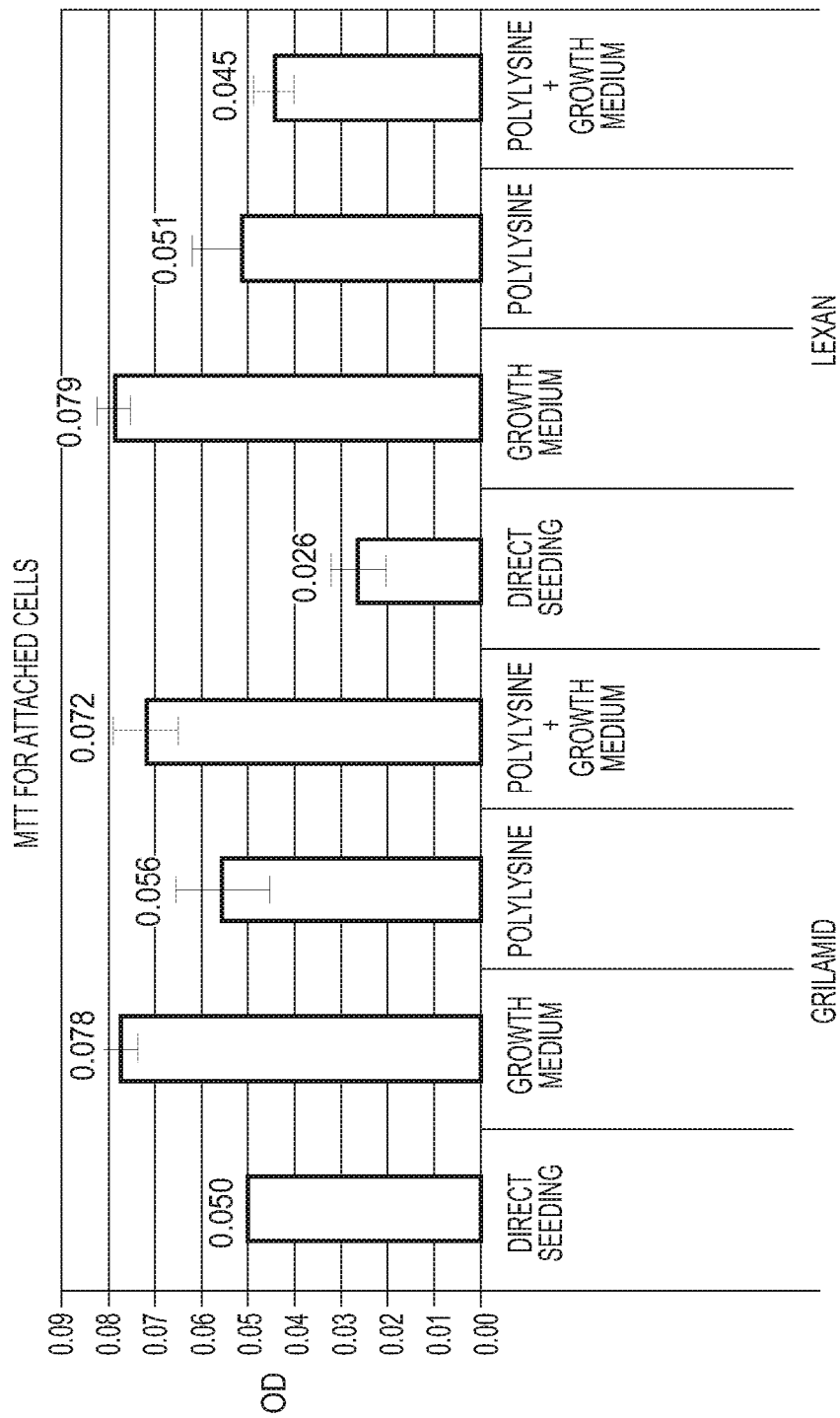
FIG. 14 is a bar graph illustrating cell attachment efficiency for cells grown using various coated two-dimensional culture devices, as described in Experiment 1.

FIG. 14 is a bar graph illustrating cell attachment efficiency for cells grown using various coated two-dimensional culture devices. The results shown in FIG. 14 are based on culture of frozen PD051010 p.3/2 cells using cell-culture devices formed of injection-moulded LEXAN® or GRIL-AMID® (as indicated in the figure) with a smooth surface texture and having a configuration as shown in FIGS. 2A-2D. Furthermore, as shown, FIG. 14 demonstrates the effect of surface treatment using growth medium proteins and/or polylysine on LEXAN® or GRILAMID® carriers. As shown, polylysine treatment and growth medium protein treatment generally increased cell attachment efficiency.

Figure 15:
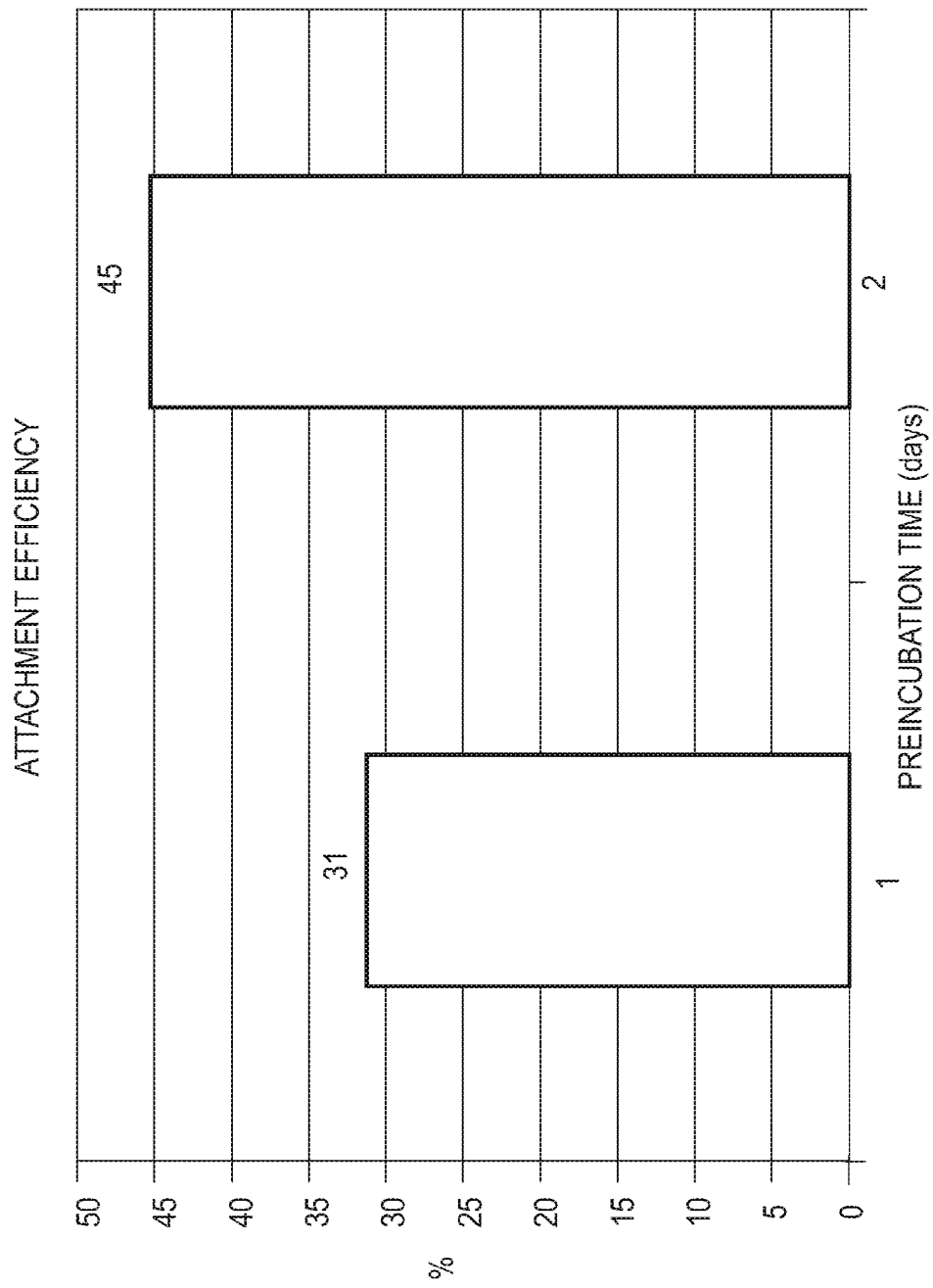
FIG. 15 is a bar graph illustrating cell attachment efficiency for cells grown using culture medium pre-incubated two-dimensional culture devices, as described in Experiment 1.

FIG. 15 is a bar graph illustrating cell attachment efficiency for cells grown using coated two-dimensional culture devices. The results shown in FIG. 15 are based on culture of frozen PD051010 p.3/2 cells using cell-culture devices formed of injection-moulded GRILAMID® with a rough surface that was preincubated with growth medium proteins and having a configuration as shown in FIGS. 1A-1B.

Figure 16:
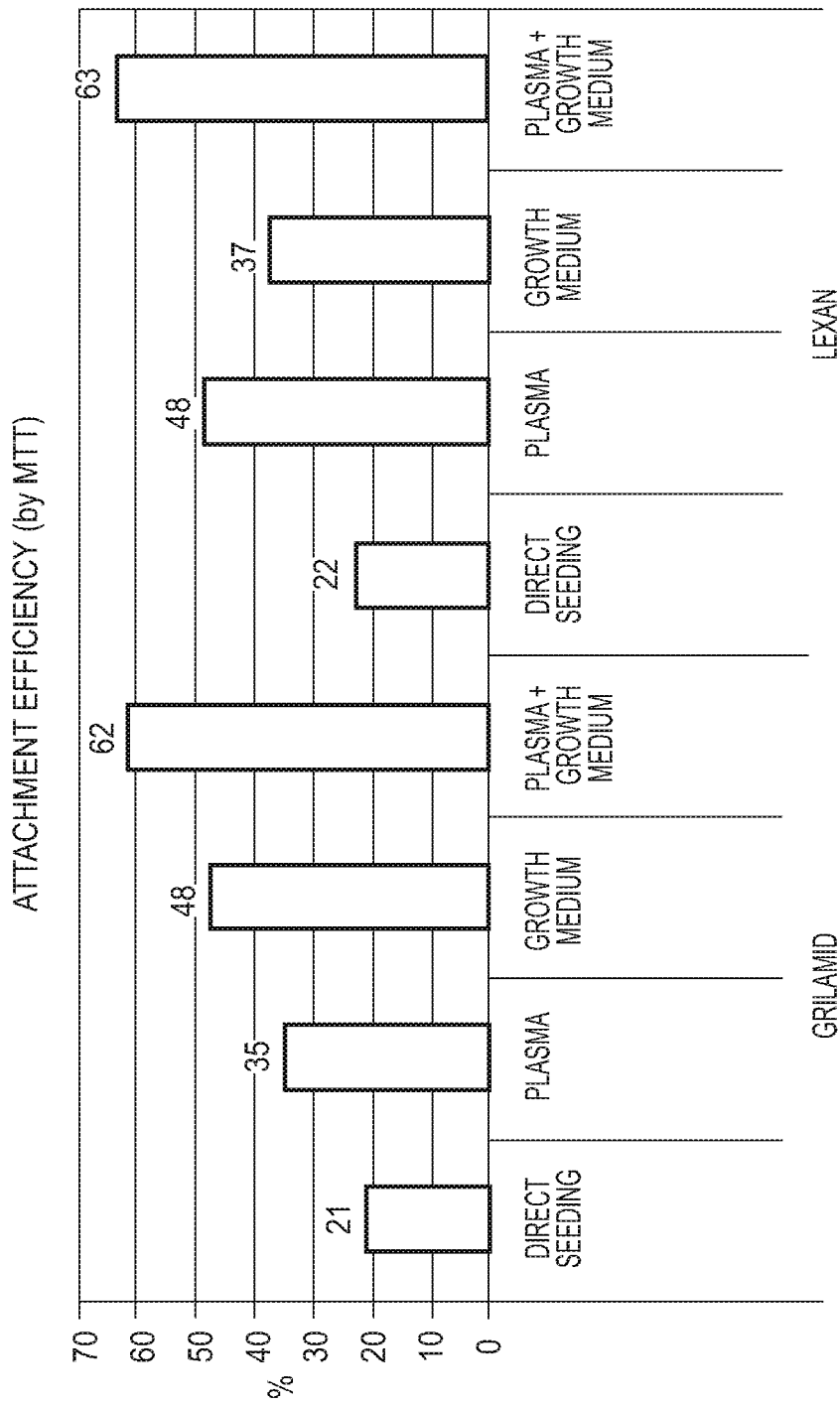
FIG. 16 is a bar graph illustrating cell attachment efficiency for cells grown using various coated two-dimensional culture devices with or without plasma surface treatment of the devices, as described in Experiment 1.

FIG. 16 is a bar graph illustrating cell attachment efficiency for cells grown using various coated two-dimensional culture devices with or without plasma surface treatment of the devices. The results shown in FIG. 16 are based on culture of frozen PD051010 p.3/2 cells using cell-culture devices formed of injection-moulded LEXAN® or GRIL-AMID® (as indicated in the figure) with a smooth surface texture and having a configuration as shown in FIGS. 2A-2D. Furthermore, as shown, FIG. 16 demonstrates the effect of surface treatment using growth medium proteins and/or plasma treatment on LEXAN® or GRILAMID® carriers. As shown, plasma treatment and growth medium protein treatment generally increased cell attachment efficiency.

Example 2

In this experiment, cells grown on two-dimensional culture devices were harvested using a vibration-based harvest method as described in PCT/IB2012/000933, filed Apr. 15, 2012. The two-dimensional culture devices were prepared by suspending 220 of the devices in Dulbeco's minimal essential medium ("DMEM") and seeding them with human placenta-derived adherent stromal cells at a concentration of 3,000 cells per cm$^2$. The devices were incubated overnight with gentle mixing to allow the cells to attach to the devices. After the overnight incubation 90-100 of the seeded devices were transferred to a 250 ml spinner flask containing 150 ml of complete DMEM and incubated at three days at 37° C. and 5% $CO_2$.

After the three day growth, cells were harvested from the devices by vibration as follows. The spinner flasks and tubes were removed from the incubator and ten of the culture devices were removed for a cell staining. Harvest efficiency was determined by cell staining and cell counts. The culture media was discarded and the remaining devices were washed twice with PBS and placed into a container filled with 800 ml of pre-warmed TrypLE solution. The devices were then immediately vibrated for 5 seconds at 5 Hz, 5 minutes at 1 Hz, and 30 seconds at 5 Hz (all at an amplitude of 25 mm). Following vibration, an additional ten devices were removed for cell staining. To the remaining devices 200 ml of FBS was added and the medium was transferred to 2,500 ml centrifuge bottles. The cells were centrifuged at 1,200 RPM for 10 minutes at 4° C., the cell pellet was resuspended, and cell counts were performed.

Harvest by vibration was shown to be an effective means of recovering cells from these devices, with 7.8×10$^6$ cells being recovered. The cells were shown to have 95% viability by trypan blue dye exclusion.

Example 3

In another experiment, Placenta (PD020112), Adipose (PLA25) and B one-marrow (BM122) MSC's were seeded on 175 cm$^2$ flasks, 0.5×10$^6$ cells/flask, in full DMEM growth medium (DMEM As22320 Cat. No. 041-96417A GIBCO, 10% FBS cat. No. 50115 BIOCHROM, 1% L-Glutamine Cat no. G7513 SIGMA). Cells were incubated in 37° C. humidified incubator for 4 days. Each cell type was harvested using TrypLE (GIBCO Cat no. 12563-029). Each cell type was then seeded on both 175 cm$^2$ flasks and on 2D carriers, in full DMEM, in duplicates. Following, 0.5×10$^6$ cells were seeded on flasks and 1×10$^6$ cells were seeded on 90 2D carriers, in 20 ml vials. The flasks were incubated in 37° C. incubator. The 2D carriers vials were rolled for 24 hours for attachment and then transferred to 250 ml spinner flask with basket. The spinners were placed on stirrer in 37° C. incubator for another 3 days, on 40 RPM stirring velocity. After total growth duration of 4 days the cells were harvested from the flasks and from the 2D carriers by TrypLE and counted by Casy cell counter.

Figure 17:
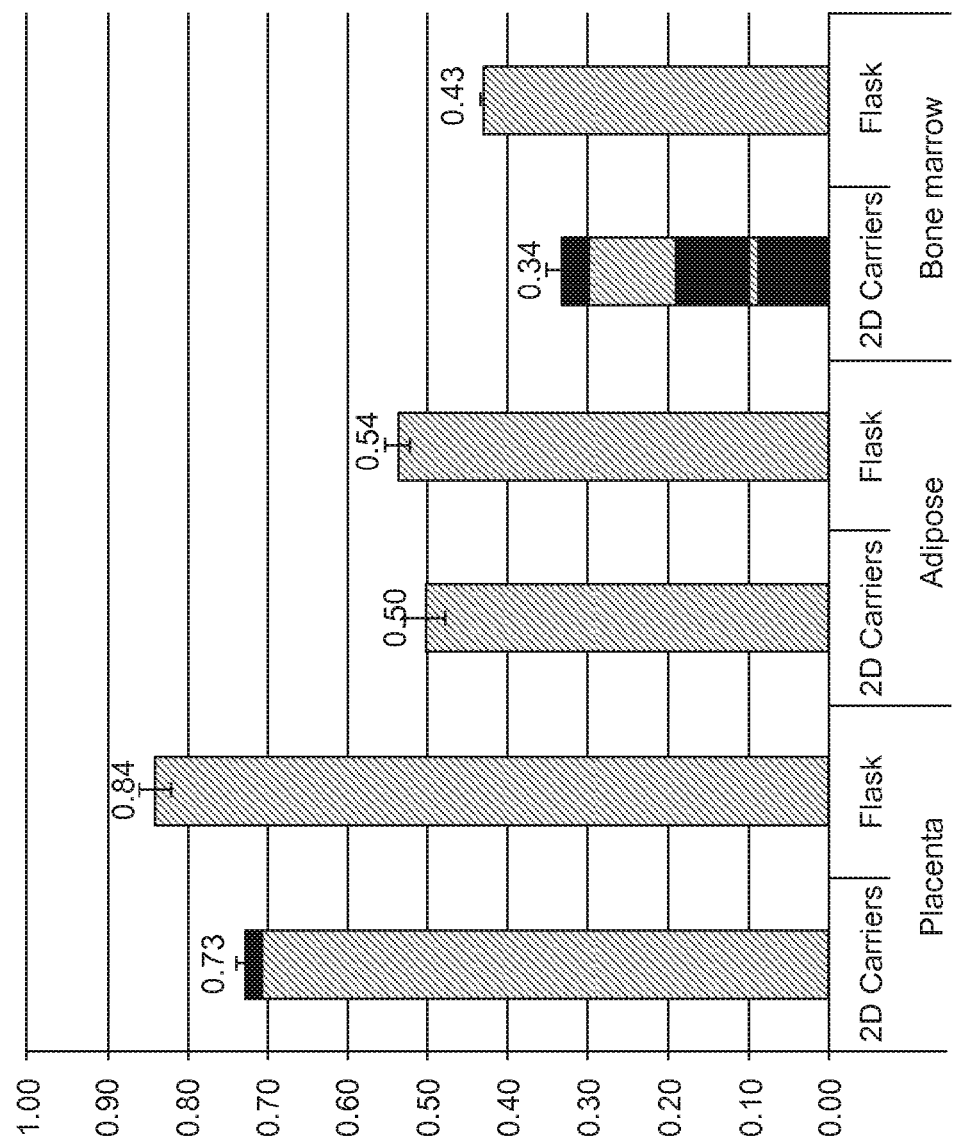
FIG. 17 is a bar graph illustrating PDD (population doubling per day) comparison between 175 $cm^2$ flasks and 2D carriers, as described in Experiment 3.

FIG. 17 shows a bar chart of PDD (population doubling per day) comparison between 175 cm² flasks and 2D carriers. The calculated PDD's show comparable growth rates of Placenta, Bone-marrow and Adipose cells between 2D carriers and flasks.

What is claimed is:

1. A cell-culture device, comprising:
a three-dimensional body comprising multiple two-dimensional surfaces extending inwardly from a periphery of the three-dimensional body towards an interior of the three-dimensional body, wherein:
(a) the multiple two-dimensional surfaces are configured to support monolayer growth of eukaryotic cells over at least a majority of or all of the surface area of the multiple two-dimensional surfaces;
(b) the multiple two-dimensional surfaces comprise a plurality of ribs extending substantially parallel to one another from the interior of the three-dimensional body towards the periphery of the three-dimensional body, further including a lateral plane extending from a central axis of the three-dimensional body and extending perpendicularly to the plurality of ribs, and wherein the plurality of ribs are spaced from one another by a width that does not exceed the thickness of any one of the plurality of ribs; and
(c) the three-dimensional body has a maximum dimension between 2 mm and 10 mm, wherein the device is substantially spherical, and wherein the maximum dimension is a diameter; or the ratio of the surface area of the multiple two-dimensional surfaces to the volume of the three-dimensional body is between 10 cm²/cm³ and 15 cm²/cm³.

2. The device of claim 1, wherein the three-dimensional body comprises at least one of a substantially spherical shape, a substantially ellipsoid shape, and an irregular polyhedral shape.

3. The device of claim 1, wherein the material forming the multiple two-dimensional surfaces comprises a material selected from at least one of metals, glass, borosilicate, carbon fibers, ceramics, collagen, gelatin, hydrogels, and polymers.

4. The device of claim 1, wherein the material forming the multiple two-dimensional surfaces comprises at least one polymer, wherein the polymer is:
selected from a polyamide, a polycarbonate, a polysulfone, a polyester, a polyacetal, and polyvinyl chloride.

5. The device of claim 1, wherein the multiple two-dimensional surfaces further comprise at least one coating selected to facilitate attachment and growth of eukaryotic cells, wherein the at least one coating is selected from a protein and polylysine.

6. The device of claim 1, wherein the multiple two-dimensional surfaces have been subjected to a plasma surface treatment.

7. The device of claim 1, wherein the multiple two-dimensional surfaces comprise a modulus and curvature selected to facilitate growth of eukaryotic cells.

8. The device of claim 1, wherein the eukaryotic cells comprise at least one of stem cells, anchorage dependent cells, mesenchymal cells, and stromal cells.

9. The device of claim 1, wherein the ratio of the surface area of the multiple two-dimensional surfaces to the volume of the three-dimensional body is between 3 cm²/cm³ and 1,000 cm²/cm³.

10. The device of claim 1, wherein the ratio of the surface area of the multiple two-dimensional surfaces to the volume of the three-dimensional body is between 10 cm²/cm³ and 15 cm²/cm³.

11. The device of claim 1, wherein the three-dimensional body has a maximum dimension between 2 mm and 10 mm, wherein the device is substantially spherical, and the maximum dimension is a diameter.

12. A cell-culture system, comprising:
a container; and
a group of three-dimensional bodies, each three dimensional body comprising:
multiple two-dimensional surfaces extending inwardly from a periphery of the three-dimensional body towards an interior of each three-dimensional body, wherein:
(a) the multiple two-dimensional surfaces are configured to support monolayer growth of eukaryotic cells over at least a majority of or all of the surface area of the multiple two-dimensional surfaces;
(b) the multiple two-dimensional surfaces comprise a plurality of ribs extending substantially parallel to one another from the interior of the three-dimensional body towards the periphery of the three-dimensional body, further including a lateral plane extending from a central axis of the three-dimensional body and extending perpendicularly to the plurality of ribs, and wherein the plurality of ribs are spaced from one another by a width that does not exceed the thickness of any one of the plurality of ribs; and
(c) the three-dimensional bodies each have: a maximum dimension ranging from 1 mm to 50 mm; or the ratio of the surface area of the multiple two-dimensional surfaces to the volume of the three-dimensional body is between 10 cm²/cm³ and 15 cm²/cm³.

13. The system of claim 12, wherein the three-dimensional bodies each have a maximum dimension between 1 mm and 20 mm.

14. The system of claim 12, wherein the material forming the multiple two-dimensional surfaces comprises at least one polymer, wherein the polymer is selected from a polyamide, a polycarbonate, a polysulfone, a polyester, a polyacetal, and polyvinyl chloride.

15. The system of claim 12, wherein the multiple two-dimensional surfaces further comprise at least one coating selected to facilitate attachment and growth of eukaryotic cells, wherein the at least one coating is selected from a protein and polylysine.

16. The system of claim 12, wherein the ratio of the surface area of the multiple two-dimensional surfaces to the volume of the three-dimensional body is between 3 cm²/cm³ and 1,000 cm²/cm³.

17. A cell-culture system, comprising:
a container; and
a group of three-dimensional bodies, each three dimensional body comprising:
multiple two-dimensional surfaces extending inwardly from a periphery of the three-dimensional body towards an interior of each three-dimensional body, wherein:
(a) the multiple two-dimensional surfaces are configured to support monolayer growth of eukaryotic cells over at least a majority of or all of the surface area of the multiple two-dimensional surfaces, and wherein the multiple two-dimensional surfaces have been subjected to a plasma surface treatment;

(b) the multiple two-dimensional surfaces comprise a plurality of ribs extending substantially parallel to one another from the interior of the three-dimensional body towards the periphery of the three-dimensional body, further including a lateral plane extending from a central axis of the three-dimensional body and extending perpendicularly to the plurality of ribs, and wherein the plurality of ribs are spaced from one another by a width that does not exceed the thickness of any one of the plurality of ribs; and (c) the three-dimensional bodies each have: a maximum dimension ranging from 1 mm to 50 mm; or a surface area to volume ratio between 3 $cm^2/cm^3$ and 1,000 $cm^2/cm^3$.

18. The system of claim 12, wherein the three-dimensional body has a maximum dimension between 2 mm and 10 mm, wherein the device is substantially spherical, and the maximum dimension is a diameter.

19. A method of culturing cells, comprising:
   selecting a group of eukaryotic cells; and
   contacting the eukaryotic cells with the at least one three-dimensional body as defined in claim 1.

20. The method of claim 19, wherein contacting the eukaryotic cells with the at least one three-dimensional body comprises:

(a) placing the cells and at least one three-dimensional body in a container;

(b) further comprising supplying culture media to the cells; and (c) further comprising causing movement of the at least one three-dimensional body, wherein causing movement comprises:

(i) rotating or shaking a container in which the at least one three-dimensional body is contained; or (ii) providing a flow of media into a container in which the at least one three-dimensional body is contained.

21. The method of claim 19, wherein said at least one three dimensional body is immersed within culture medium inside a suitable container which is configured to resist cellular adhesion.

22. A method of culturing cells, comprising:
   selecting a group of eukaryotic cells; and
   contacting the eukaryotic cells with the cell-culture system as defined in claim 12.

23. The system of claim 17, wherein the ratio of the surface area of the multiple two-dimensional surfaces to the volume of the three-dimensional body is between 10 $cm^2/cm^3$ and 15 $cm^2/cm^3$.

* * * * *